(12) United States Patent
Priebe

(10) Patent No.: US 8,067,637 B2
(45) Date of Patent: Nov. 29, 2011

(54) CONTRAST AGENTS

(75) Inventor: Hanno Priebe, Oslo (NO)

(73) Assignee: GE Healthcare AS, Oslo (NO)

( * ) Notice: Subject to any disclaimer, the term of this patent is extended or adjusted under 35 U.S.C. 154(b) by 757 days.

(21) Appl. No.: 12/279,095

(22) PCT Filed: Feb. 13, 2007

(86) PCT No.: PCT/NO2007/000045
§ 371 (c)(1),
(2), (4) Date: Aug. 12, 2008

(87) PCT Pub. No.: WO2007/094677
PCT Pub. Date: Aug. 23, 2007

(65) Prior Publication Data
US 2009/0028799 A1 Jan. 29, 2009

(30) Foreign Application Priority Data

Feb. 14, 2006 (NO) .................................. 20060722
May 11, 2006 (NO) .................................. 20062123

(51) Int. Cl.
*C07C 233/05* (2006.01)
*A61K 49/04* (2006.01)
(52) U.S. Cl. .................................. 564/153; 424/9.452
(58) Field of Classification Search .................. 564/153; 424/9.452
See application file for complete search history.

(56) References Cited

U.S. PATENT DOCUMENTS 3,781,338 A    12/1973  Wiegert
5,851,511 A *  12/1998  Le Lem et al. ............. 424/9.452

FOREIGN PATENT DOCUMENTS

WO    95/01966    1/1995

OTHER PUBLICATIONS

Felder E., et.al. Farmaco, Edizione Scientifica, vol. 28, No. 11, 1973 pp. 912-924.
Weichert, J.P., et.al. "Potential tumor or organ-imaging agents. 27. polyiodinated 1,3-disubstituted and 1,2,3-trisubstituted triacylglycerols" Journal of Medicinal Chemistry, vol. 29, No. 12, 1986, pp. 2457-2465.
PCT/NO2007/000045 Int'l Search Report/Written Opinion dated Jun. 2007.

* cited by examiner

*Primary Examiner* — Shailendra Kumar

(57) ABSTRACT

The present invention relates to a class of compounds and to diagnostic compositions containing such compounds where the compounds are iodine containing compounds. More specifically the iodine containing compounds are chemical compounds containing a hydrophilic aliphatic central moiety allowing for the arrangement of three iodinated phenyl groups bound thereto. The invention also relates to the use of such diagnostic compositions as contrast agents in diagnostic imaging and in particular in X-ray imaging and to contrast media containing such compounds.

19 Claims, No Drawings

CONTRAST AGENTS

This application is a filing under 35 U.S.C. 371 of international application number PCT/NO2007/000045, filed Feb. 13, 2007, which claims priority to application number 20060722 filed Feb. 14, 2006 and 20062123 filed May 11, 2006, in Norway the entire disclosure of which is hereby incorporated by reference.

TECHNICAL FIELD OF THE INVENTION

The present invention relates to a class of compounds and to diagnostic compositions containing such compounds where the compounds are iodine containing compounds. More specifically the iodine containing compounds are chemical compounds containing a hydrophilic aliphatic central moiety allowing for the arrangement of three or four iodinated phenyl groups bound thereto.

The invention also relates to the use of such diagnostic compositions as contrast agents in diagnostic imaging and in particular in X-ray imaging and to contrast media containing such compounds.

DESCRIPTION OF RELATED ART

All diagnostic imaging is based on the achievement of different signal levels from different structures within the body. Thus in X-ray imaging for example, for a given body structure to be visible in the image, the X-ray attenuation by that structure must differ from that of the surrounding tissues. The difference in signal between the body structure and its surroundings is frequently termed contrast and much effort has been devoted to means of enhancing contrast in diagnostic imaging since the greater the contrast between a body structure and its surroundings the higher the quality of the images and the greater their value to the physician performing the diagnosis. Moreover, the greater the contrast the smaller the body structures that may be visualized in the imaging procedures, i.e. increased contrast can lead to increased spatial resolution.

The diagnostic quality of images is strongly dependent on the inherent noise level in the imaging procedure, and the ratio of the contrast level to the noise level can thus be seen to represent an effective diagnostic quality factor for diagnostic images.

Achieving improvement in such a diagnostic quality factor has long been and still remains an important goal. In techniques such as X-ray, magnetic resonance imaging (MRI) and ultrasound, one approach to improving the diagnostic quality factor has been to introduce contrast enhancing materials formulated as contrast media into the body region being imaged.

Thus in X-ray early examples of contrast agents were insoluble inorganic barium salts which enhanced X-ray attenuation in the body zones into which they distributed. For the last 50 years the field of X-ray contrast agents has been dominated by soluble iodine containing compounds. Commercial available contrast media containing iodinated contrast agents are usually classified as ionic monomers such as diatrizoate (marketed e.g. under the trade name Gastrografen™), ionic dimers such as ioxaglate (marketed e.g. under the trade name Hexabrix™), nonionic monomers such as iohexol (marketed e.g. under the trade name Omnipaque™), iopamidol (marketed e.g. under the trade name Isovue™), iomeprol (marketed e.g. under the trade name Iomeron™) and the non-ionic dimer iodixanol (marketed under the trade name and Visipaque™).

The most widely used commercial non-ionic X-ray contrast agents such as those mentioned above are considered safe. Contrast media containing iodinated contrast agents are used in more that 20 millions of X-ray examinations annually in the USA and the number of adverse reactions is considered acceptable. However, since a contrast enhanced X-ray examination will require up to about 200 ml contrast media administered in a total dose, there is a continuous drive to provide improved contrast media.

The utility of the contrast media is governed largely by its toxicity, by its diagnostic efficacy, by adverse effects it may have on the subject to which the contrast medium is administered, and by the ease of storage and ease of administration. Since such media are conventionally used for diagnostic purposes rather than to achieve direct therapeutic effect, it is generally desirable to provide media having as little as possible effect on the various biological mechanisms of the cells or the body as this will lead to lower toxicity and lower adverse clinical effect. The toxicity and adverse biological effects of a contrast medium are contributed to by the components of the formulation medium, e.g. the solvent or carrier as well as the contrast agent itself and its components such as ions for the ionic contrast agents and also by its metabolites.

The major contributing factors to the toxicity of the contrast medium are identified as the chemotoxicity of the contrast agent, the osmolality of the contrast medium and the ionic composition or lack thereof of the contrast medium.

Desirable characteristics of an iodinated contrast agent are low toxicity of the compound itself (chemotoxicity), low viscosity of the contrast medium wherein the compound is dissolved, low osmolality of the contrast medium and a high iodine content (frequently measured in g iodine per ml of the formulated contrast medium for administration). The iodinated contrast agent must also be completely soluble in the formulation medium, usually an aqueous medium, and remain in solution during storage.

The osmolalities of the commercial products, and in particular of the non-ionic compounds is acceptable for most media containing dimers and non-ionic monomers although there is still room for improvement. In coronary angiography for example, injection into the circulatory system of a bolus dose of contrast medium has caused severe side effects. In this procedure contrast medium rather than blood flows through the system for a short period of time, and differences in the chemical and physiochemical nature of the contrast medium and the blood that it replaces can cause undesirable adverse effects such as arrhythmias, QT prolongation and reduction in cardiac contractive force. Such effects are seen in particular with ionic contrast agents where osmotoxic effects are associated with hypertonicity of the injected contrast medium. Contrast media that are isotonic or slightly hypotonic with the body fluids are particularly desired. Low osmolar contrast media have low renal toxicity which is particularly desirable.

The osmolality is a function of the number of particles per volume unit of the formulated contrast medium.

To keep the injection volume of the contrast media as low as possible it is highly desirable to formulate contrast media with high concentration of iodine/ml, and still maintain the osmolality of the media at a low level, preferably below or close to isotonicity. The development of non-ionic monomeric contrast agents and in particular non-ionic bis(triiodophenyl) dimers such as iodixanol (EP patent 108638) has provided contrast media with reduced osmotoxicity allowing contrast effective iodine concentration to be achieved with hypotonic solution, and has even allowed correction of ionic imbalance by inclusion of plasma ions while still maintaining the contrast medium Visipaque™ at the desired osmolality (WO 90/01194 and WO 91/13636).

The X-ray contrast media at commercial high iodine concentration have relative high viscosity, ranging from about 15 to about 60 mPas at ambient temperature. Generally, contrast media where the contrast enhancing agent is a dimer has higher viscosity than the corresponding contrast media where the contrast enhancing agent is the monomer corresponding to the dimer. Such high viscosities may pose problems to the administrators of the contrast medium, requiring relatively large bore needles or high applied pressure, and are particularly pronounced in pediatric radiography and in radiographic techniques which require rapid bolus administration, e.g. in angiography.

X-ray contrast agents of high molecular weight has been proposed, e.g. polymers with substituted triiodinated phenyl groups grafted on the polymer, see EP 354836, EP 436316 and U.S. Pat. No. 5,019,370. Further, WO 9501966, EP 782563 and U.S. Pat. No. 5,817,873 read on compounds having e.g. 3 and 4 substituted triiodinated phenyl groups arranged linearly or around a central core. However, none of these proposed compounds are on the market.

Hence there still exists a desire to develop contrast agents that solves one or more of the problems discussed above. Such agents should ideally have improved properties over the soluble iodine containing compounds in one or more of the following properties: renal toxicity, osmolality, viscosity, solubility, injection volumes/iodine concentration and attenuation/radiation dose.

SUMMARY OF THE INVENTION

The present invention provides compounds useful as contrast media having improved properties over the known media with regards to at least one of the following criteria osmolality (and hence the renal toxicity), viscosity, iodine concentration and solubility. The contrast media comprises iodine containing contrast enhancing compounds where iodine containing compounds are chemical compounds containing a central hydrophilic aliphatic moiety, allowing for the arrangement of three or four iodinated phenyl groups bound to thereto. The iodine containing contrast enhancing compounds can be synthesized from commercially available and relatively inexpensive starting materials.

DETAILED DESCRIPTION OF THE INVENTION

The contrast enhancing compounds are synthetic chemical compounds of formula (I)

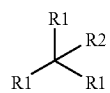

Formula (I)

wherein
each $R^1$ are the same or different and denote the moieties $CH_2$—O—$CH_2$—$R^3$;
$R^2$ denote $R^1$ or one of the moieties $C_1$-$C_4$ alkyl, $CH_2O$ ($C_1$-$C_4$ alkyl), and OH, where the alkyl group may carry one or more hydroxy groups;
each $R^3$ are the same or different and denote a $C_1$-$C_4$ alkylene moiety having α-hydroxy and ω-$NR^4$ R substituents and where the alkylene group may be further hydroxylated;
each $R^4$ are the same or different and denotes a hydrogen atom or an acyl moiety; and
each R independently are the same or different and denote a triiodinated phenyl group, preferably a 2,4,6 triiodinated phenyl group, further substituted by a group two groups $R^5$ wherein each $R^5$ are the same or different and denotes a hydrogen atom or a non-ionic hydrophilic moiety, provided that at least one $R^5$ group in the compound of formula (I) is a hydrophilic moiety;
and salts or optical active isomers thereof.

In formula (I) each of the three groups $R^1$ are preferably the same. When $R^2$ denotes $R^1$ then all four $R^1$ groups are preferably the same.

The group $R^2$ preferably denote a methyl group, an ethyl group or a hydroxylated ether group e.g. of the formula —$CH_2$—O—$CH_2$—CH(OH)—$CH_2OH$.

The group $R^3$ preferably denotes a group of formula —CH(OH)—$CH_2$—$NR^4$ R wherein $R^4$ and R have the meanings above and are preferably the same in all $R^1$ moieties in formula (I).

The group $R^4$ may also be the same or different. In a preferred embodiment each $R^4$ group may independently of each other denote residues of aliphatic organic acids, and in particular residues of aliphatic organic acids of 1 to 5 carbon atoms such as the formic, acetyl, propionyl, butyryl, isobutyryl and valeriyl moieties. Hydroxylated acyl moieties are also feasible. In a further preferred embodiment all $R^4$ groups are the same. In a particular preferred embodiment all $R^4$ groups are the same and denote the acetyl moiety.

The non-ionic hydrophilic moieties $R^5$ may be any of the non-ionizing groups conventionally used to enhance water solubility. Suitable groups include esters, amides and amine moieties that may be further substituted. Further substituents include straight chain or branched chain $C_{1-10}$ alkyl groups, preferably $C_{1-5}$ alkyl groups, optionally with one or more $CH_2$ or CH moieties replaced by oxygen or nitrogen atoms and optionally substituted by one or more groups selected from oxo, hydroxyl, amino or carboxyl derivative, and oxo substituted sulphur and phosphorus atoms. Particular examples include polyhydroxyalkyl, hydroxyalkoxyalkyl and hydroxypolyalkoxyalkyl and such groups attached to the phenyl group via an amide linkage such as hydroxyalkylaminocarbonyl, N-alkyl-hydroxyalkylaminocarbonyl and bis-hydroxyalkylaminocarbonyl groups.

In a preferred embodiment the hydrophilic moieties contain 1 to 6 hydroxy groups, preferably 1 to 3 hydroxy groups.

The $R^5$ groups of the formulas listed below are preferred:
—CONH—$CH_2$—$CH_2$—OH
—CONH—$CH_2$—CHOH—$CH_2$—OH
—CON($CH_3$)$CH_2$—CHOH—$CH_2$OH
—CONH—CH—($CH_2$—OH)$_2$
—CON—($CH_2$—$CH_2$—OH)$_2$
—$CONH_2$
—$CONHCH_3$
—$NHCOCH_2OH$
—N($COCH_3$)H
—N($COCH_3$)$C_{1-3}$ alkyl
—N($COCH_3$)— mono, bis or tris-hydroxy $C_{1-4}$ alkyl
—N($COCH_2OH$)— hydrogen, mono, bis or tris-hydroxy $C_{1-4}$ alkyl
—N(CO—CHOH—CH2OH)— hydrogen, mono, bis or trihydroxylated $C_{1-4}$ alkyl.
—N(CO—CHOH—CHOH—CH2OH)— hydrogen, mono, bis or trihydroxylated $C_{1-4}$ alkyl.
—N($COCH_2OH$)$_2$
—CON($CH_2$—CHOH—$CH_2$—OH) ($CH_2$—$CH_2$—OH)
—CONH—C($CH_2$—OH)$_3$ and
—CONH—CH($CH_2$—OH) (CHOH—$CH_2$—OH).

More preferably the $R^5$ groups will be equal or different and denote one or more moieties of the formulas —CON($CH_3$)$CH_2$—CHOH—$CH_2$OH, —CONH—$CH_2$—CHOH—$CH_2$—OH, —CONH—CH—($CH_2$—OH)$_2$, —CON—($CH_2$—$CH_2$—OH)$_2$ or —CONH—$CH_2$—CHOH—$CH_2$—OH, —$NHCOCH_2OH$ and —N($COCH_2OH$)— mono, bis or tris-hydroxy $C_{1-4}$ alkyl, and even more preferably all R groups are equal and denote one of these moieties.

Thus preferred structures according to the invention include the compounds of formulas (IIa), to (IIh):

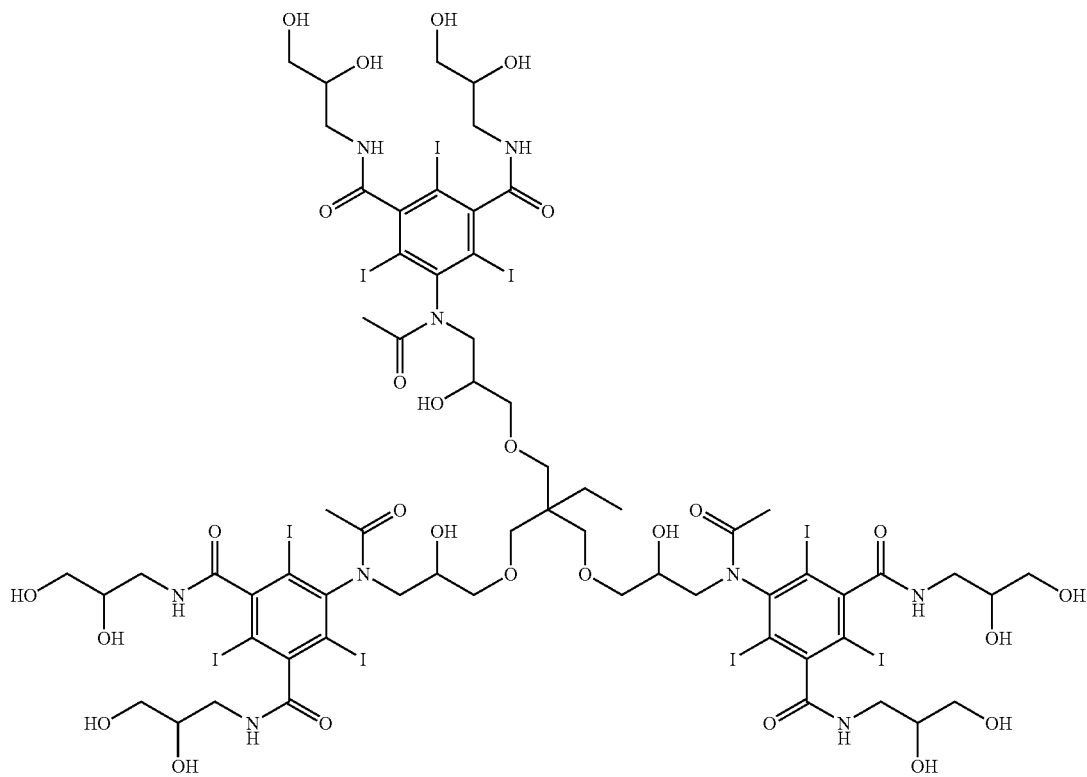

Formula (IIa) - compound of Example 1

Formula (IIb) - compound of Example 2
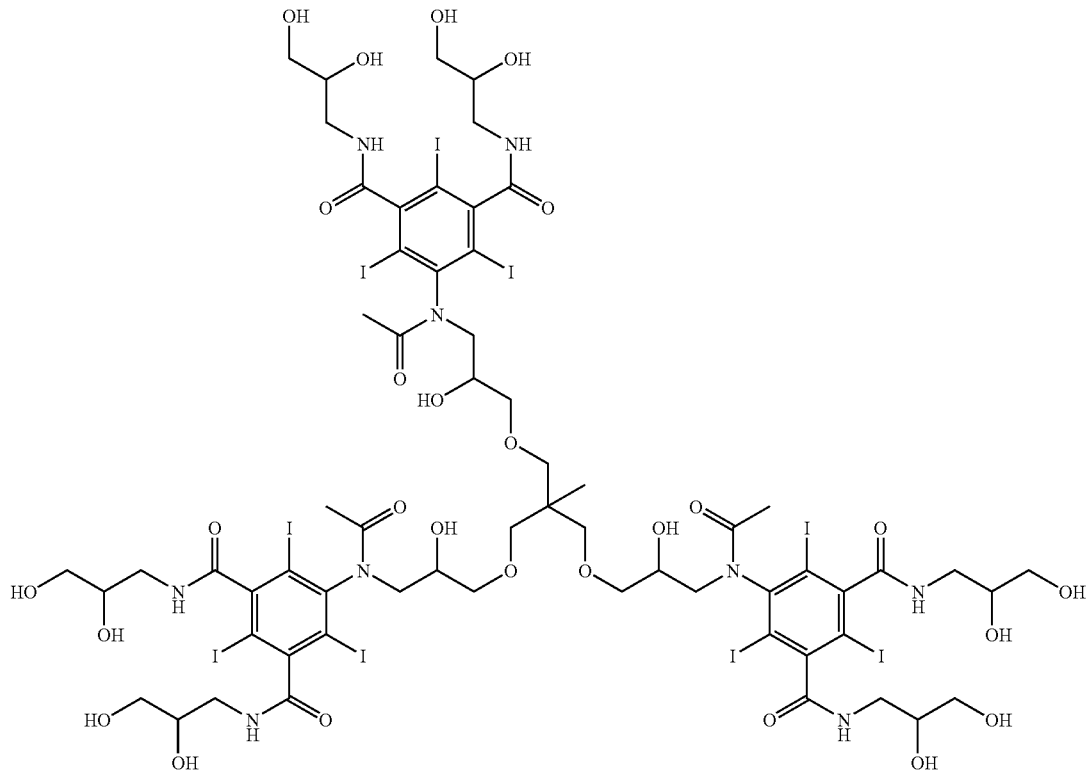
Formula (IIc) - compound of Example 3
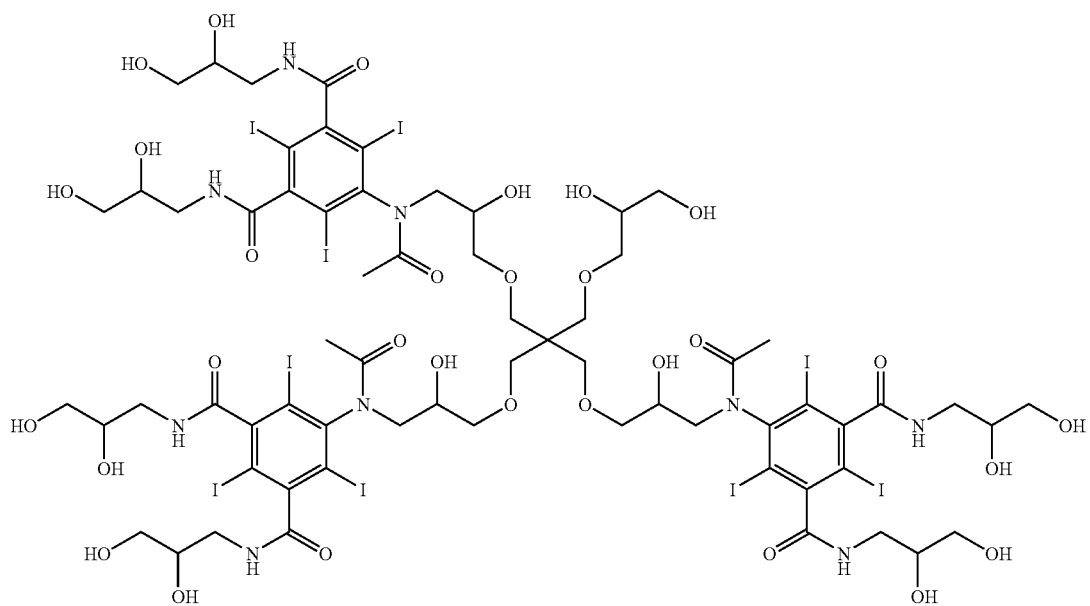

Formula (IId) - compound of Example 4
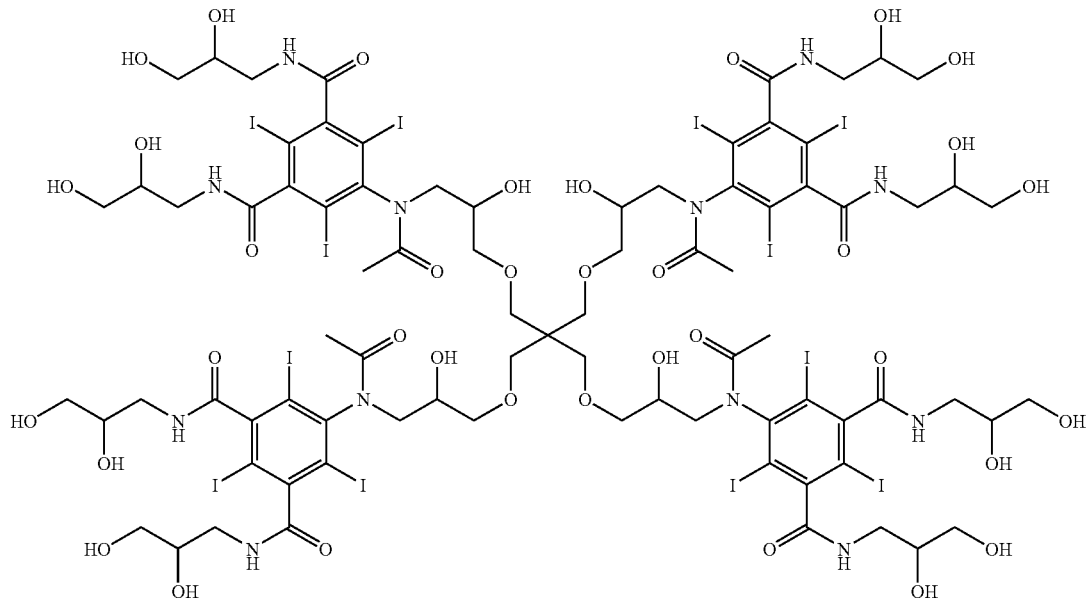
Formula (IIe)
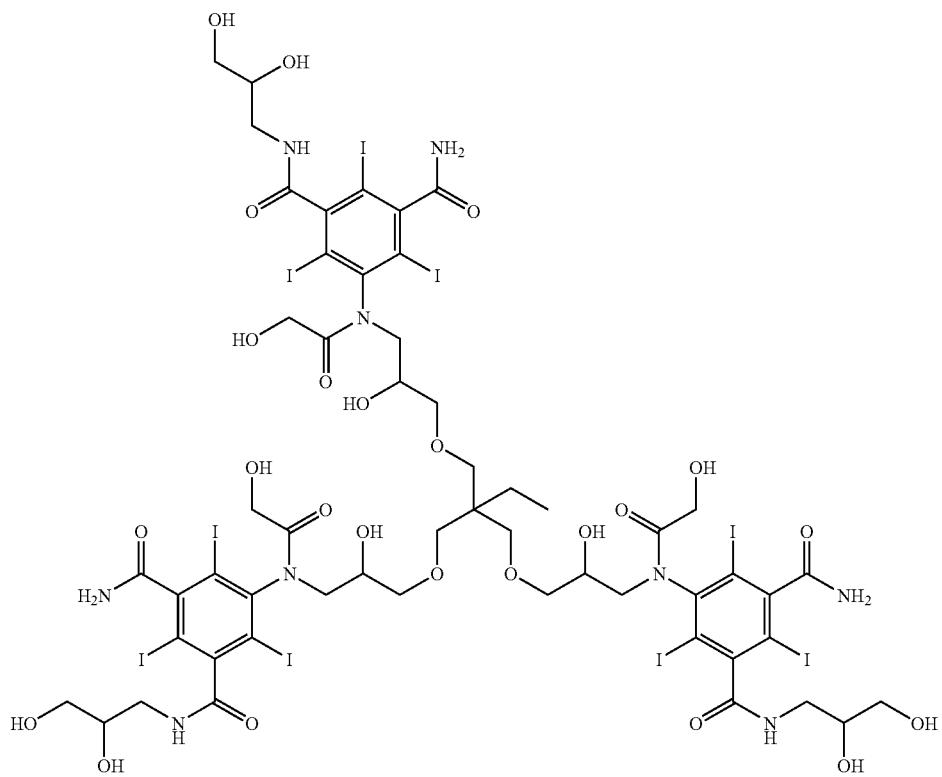
MW = 2369,33
Exact Mass = 2368,58
Formula = C54H68I9N9O24
Composition = C 27.37% H 2.89% I 48.21% N 5.32% O 16.21%

-continued
Formula (IIf)
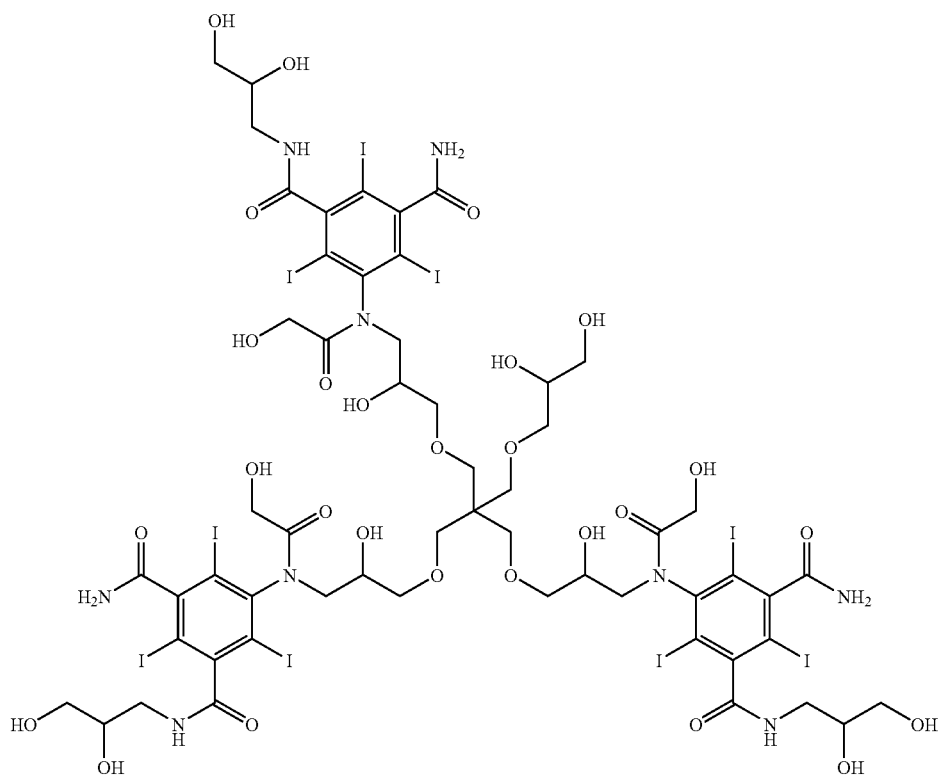
MW = 2445,38
Exact Mass = 2444,59
Formula = C56H72I9N9O27
Composition = C 27.51% H 2.97% I 46.71% N 5.16% O 17.67%
Formula (IIg)
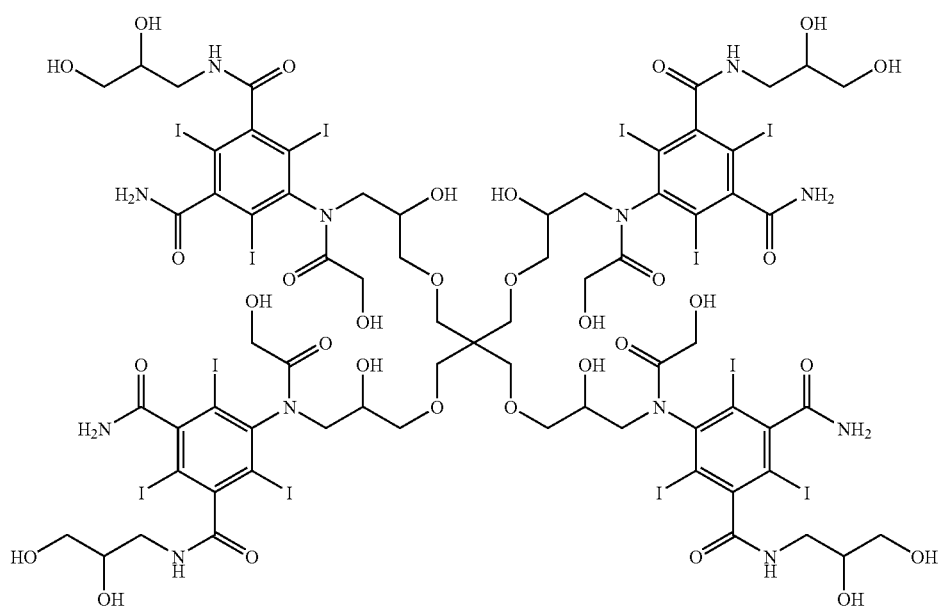
MW = 3116,35
Exact Mass = 3115,39
Formula = C69H84I12N12O32
Composition = C 26.59% H 2.72% I 48.87% N 5.39% O 16.43%

-continued

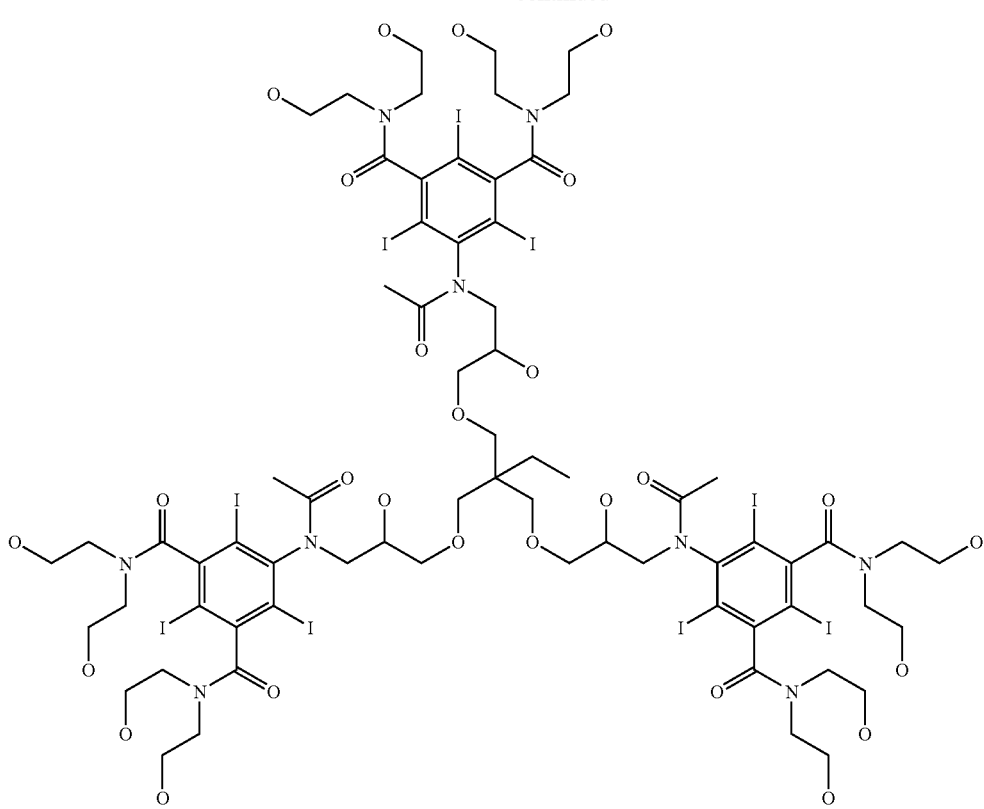

Formula (IIh)

The compounds of formula (I) will attain a star-form with the relatively bulky iodinated phenyl substituents filling up the area between the 3 or 4 arms of the star. The molecule will therefore adopt a relatively round or globular form. Globular molecules will usually have enhanced solubility compared with similar molecules with a more planar structure.

At an iodine concentration of 320 mg/ml, which is a common concentration for commercially available iodinated contrast media, the concentration of the compound of formula (I) will be approximately 0.28 M (Molar) for compounds with 3 iodinated aryl groups and approximately 0.21 M for compounds with 4 iodinated aryl groups. The contrast medium will also be hypoosmolar at this iodine concentration, and this is an advantageous property with regards to the nephrotoxicity of the contrast medium. It is also possible to add electrolytes to the contrast medium to lower the cardiovascular effects as explained in WO 90/01194 and WO 91/13636.

Compounds of formula (I) also comprises optical active isomers. Both enantiomerically pure products as well as mixtures of optical isomers are included.

The compounds of the invention may be used as contrast agents and may be formulated with conventional carriers and excipients to produce diagnostic contrast media.

Thus viewed from a further aspect the invention provides a diagnostic agent and in particular a X-ray diagnostic agent comprising a compound of formula (I) as described above.

Further, the invention provides a diagnostic composition comprising a diagnostic agent and in particular a X-ray diagnostic agent, of a compound of formula (I) as described above together with at least one physiologically tolerable carrier or excipient, e.g. in aqueous solution for injection optionally together with added plasma ions or dissolved oxygen.

Still further, the invention provides a use of the diagnostic agent and the diagnostic composition containing a compound of formula (I) and use of the compounds for the manufacture of a contrast agent for use in diagnostic imaging, in particular in X-ray imaging.

Methods of diagnosis and methods of imaging, specifically X-ray imaging, are also provided, which comprises the administration of compounds of formula (I) to the human or animal body, examining the body with a diagnostic device and compiling data from the examination, and optionally analysing the data and reaching to a diagnosis. Alternatively, in the method of diagnosis the human and animal body are preadministered with the compounds of formula (I).

The diagnostic composition of the invention may be in a ready to use form of a suitable concentration or may be a concentrate form for dilution prior to administration. Generally compositions in a ready to use form will have iodine concentrations of at least 100 mg I/ml, preferably at least 150 mg I/ml, with concentrations of at least 300 mg I/ml, e.g. 320 mg I/ml being preferred. The higher the iodine concentration, the higher is the diagnostic value in the form of X-ray attenuation of the contrast media. However, the higher the iodine concentration the higher is the viscosity and the osmolality of the composition. Normally the maximum iodine concentration for a given contrast media will be determined by the solubility of the contrast enhancing agent, e.g. the iodinated compound, and the tolerable limits for viscosity and osmolality.

For contrast agent compositions or media which are administered by injection or infusion, the desired upper limit for the solution's viscosity at ambient temperature (20° C.) is about 30 mPas, however viscosities of up to 50 to 60 mPas and even more than 60 mPas can be tolerated. For contrast media given by bolus injection, e.g. in angiographic procedures, osmotoxic effects must be considered and preferably the osmolality should be below 1 Osm/kg $H_2O$, preferably below 850 mOsm/kg $H_2O$ and more preferably about 300 mOsm/kg $H_2O$.

With the compounds of the invention such viscosity, osmolality and iodine concentrations targets can be met. Indeed, effective iodine concentrations can be reached with hypotonic solutions. It may thus be desirable to make up the solution's tonicity by the addition of plasma cations so as to reduce the toxicity contribution that derives from the imbalance effects following bolus injection. Such cations will desirably be included in the ranges suggested in WO 90/01194 and WO 91/13636.

In particular, addition of sodium and calcium ions to provide a contrast medium isotonic with blood for all iodine concentrations is desirable and obtainable. The plasma cations may be provided in the form of salts with physiologically tolerable counterions, e.g. chloride, sulphate, phosphate, hydrogen carbonate etc., with plasma anions preferably being used.

The compounds of the general formula (I) can be synthesized from triepoxide or tetraepoxide derivatives and triiodinated phenyl compounds having a reactive amine function in a one step process. Some triepoxides and tetraepoxides are commercially available or can be produced from epichlorohydrin and triols or tetraols according to the procedure of T. Kida, M. Yokota, A. Masuyama, Y. Nakatsuji, M. Okahara: A facile synthesis of polyglycidyl ethers from polyols and epichlorohydrin. Synthesis, (5) 1993, 487-489. Examples of triepoxides and tetraepoxides are compounds of the formulas:

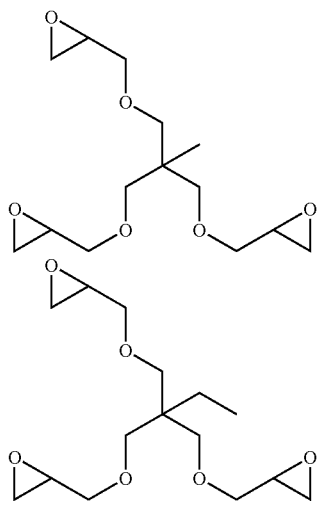

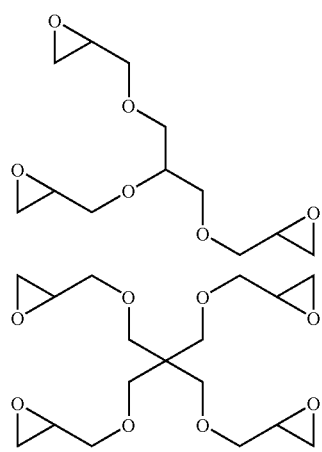

Tri-iodinated phenyl groups are commercially available or can be produced following procedures described or referred to e.g. in WO95/35122 and WO98/52911. The preferred tri-iodinated compound 5-amino-2,4,6-triiodo-N,N'-bis(2,3-dihydroxypropyl)-isophtalamide is commercially available e.g. from Fuji Chemical Industries, Ltd. The production of 5-N-acetylated compounds and corresponding acylated compounds can be effected by any conventional acylation agent such as acetylation with acetic acid anhydride, as described in U.S. Pat. No. 4,250,113.

The acylamino-triiodophenyl derivate is dissolved in aqueous methanol in presence of alkali hydroxide. Optionally the start pH can be adjusted with boric acid before addition of the tri-epoxide. The reaction is stopped by neutralisation to pH<7 and the product is isolated by preparative HPLC.

The general procedure can be illustrated by the schemes below, where compounds of formula (II) are produced:

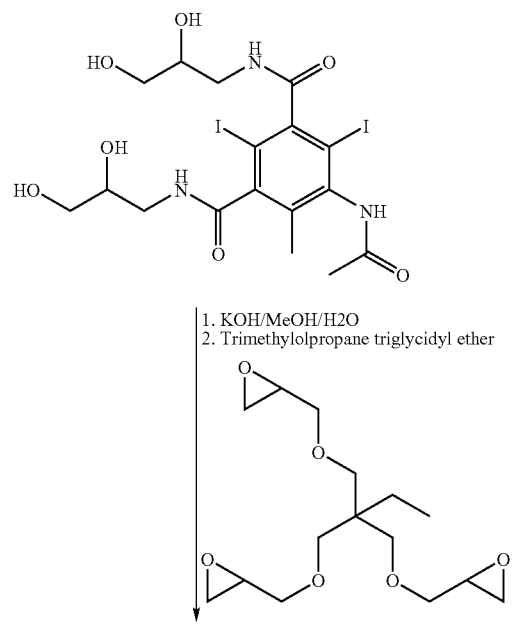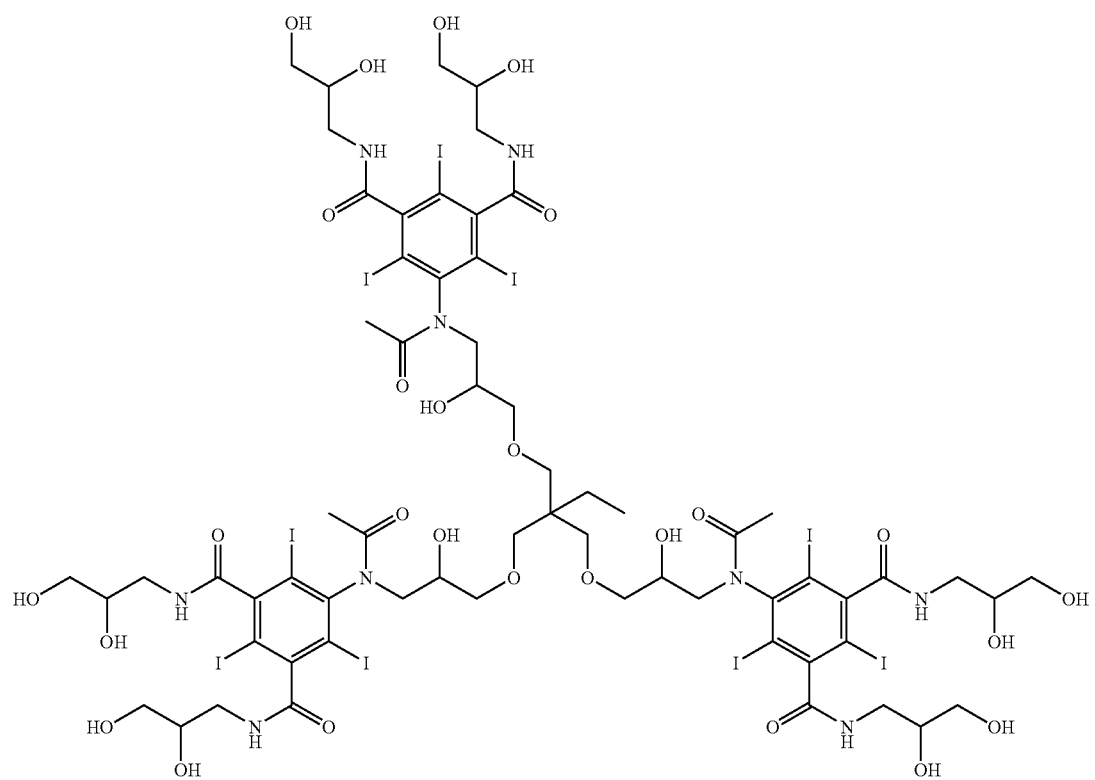

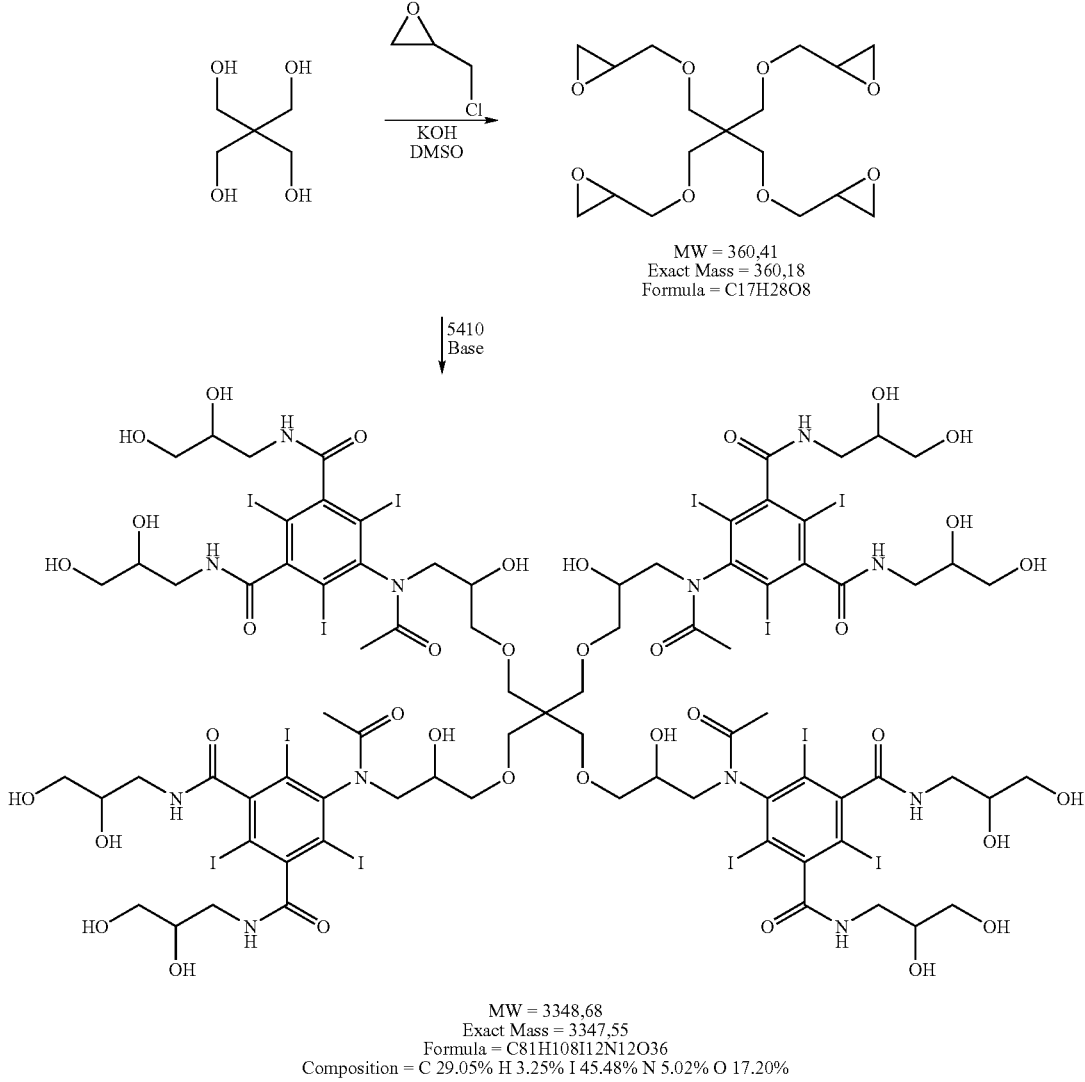

MW = 360,41
Exact Mass = 360,18
Formula = C17H28O8

5410
Base

MW = 3348,68
Exact Mass = 3347,55
Formula = C81H108I12N12O36
Composition = C 29.05% H 3.25% I 45.48% N 5.02% O 17.20%

The invention will hereinafter be further illustrated with non-limiting examples.

EXAMPLE 1

5-(Acetyl-{3-[2,2-bis-(3-{acetyl-[3,5-bis-(2,3-dihydroxy-propylcarbamoyl)-2,4,6-triiodo-phenyl]-amino}-2-hydroxy-propoxymethyl)-butoxy]-2-hydroxy-propyl}-amino)-N,N'-bis-(2,3-dihydroxy-propyl)-2,4,6-triiodo-isophthalamide Trimethylolpropane triglycidylether was commercial available from Aldrich. At 23-50° C. 5-Acetylamino-N,N'-bis-(2,3-dihydroxy-propyl)-2,4,6-triiodo-isophthalamide (500 g, 669 mmol) was dissolved in a solution of KOH (53,76 g, 958 mmol) in water (539 ml) and methanol (254 ml). To the clear solution boric acid (36.05 g, 583 mmol) is added and stirred for 0.5-3 h. At 23-25° C. Trimethylolpropane triglycidylether (34.14 g, 112.9 mmol) was added and stirred for 2 d. The reaction was stopped by adding water (900 ml) and neutralization with 18.4% aqueous HCl to pH 4-5. A white precipitate (starting material) was filtered and the filtercake washed with water. Salts were removed from the filtrate by ion exchangers Amberlite 200C and IRA67. The solution contains 28 HPLC area % target compound (ca. 80 g) and the product was isolated by prep. HPLC.

HPLC/MS (TOF ES+, m/e): 2543,8 $[M+H]^+$, 1272,4 $[M+2H]^{2+}$.

$^1$H NMR (d6-DMSO): 8,7-8,1 (m, 6H, NH), 4,9-4,4 (m, 15H, OH+CH), 4,0-3,0 (m, $CH_2$, CH), 2,2 & 1,8 (s, 9H, $CH_3$—CO), 1,4 (m, 2H, C—$CH_2$), 0,8 (t, 3H, $CH_3$).

IR: 3262 (m), 2927 (w), 2874 (w), 1638 (s), 1546 (m), 1394 (m), 1253 (m), 1105 (m), 1036 (s), 978 (w).

EXAMPLE 2

5-(Acetyl-{3-[2,2-bis-(3-{acetyl-[3,5-bis-(2,3-dihydroxy-propylcarbamoyl)-2,4,6-triiodo-phenyl]-amino}-2-hydroxy-propoxymethyl)-propoxy]-2-hydroxy-propyl}-amino)-N,N'-bis-(2,3-dihydroxy-propyl)-2,4,6-triiodo-isophthalamide The triepoxide trimethylolethane triglycidylether was prepared according to the procedure of T. Kida, M. Yokota, A. Masuyama, Y. Nakatsuji, M. Okahara: A facile synthesis of polyglycidyl ethers from polyols and epichlorohydrin. Synthesis, (5) 1993, 487-489. At 23-50° C. 5-Acetylamino-N,N'-bis-(2,3-dihydroxy-propyl)-2,4,6-triiodo-isophthalamide (500 g, 669 mmol) was dissolved in a solution of KOH (49.08 g, 874 mmol) in water (537 ml) and methanol (253 ml). To the clear solution boric acid (26.81 g, 433 mmol) was added and stirred for 0.5-3 h. At 10° C. Trimethylolethane triglycidylether (32.4 g, 112.4 mmol) was added and stirred for 2 d. The reaction was stopped by adding water (1000 ml) and neutralization with 18.4% aqueous HCl to pH 4-5. A white precipitate (starting material) was filtered and the filter cake washed with water. Salts were removed from the filtrate by ion exchangers Amberlite 200C and IRA67. The solution contains 40 HPLC area% target compound (ca. 110 g) and the product was isolated by prep. HPLC.

HPLC/MS (TOF ES+, m/e): 2529,9 $[M+H]^+$, 1265,4 $[M+2H]^{2+}$.

EXAMPLE 3

5-(Acetyl-{3-[2,2-bis-(3-{acetyl-[3,5-bis-(2,3-dihydroxy-propylcarbamoyl)-2,4,6-triiodo-phenyl]-amino}-2-hydroxy-propoxymethyl)-3-(2,3-dihydroxy-propoxy)-propoxy]-2-hydroxy-propyl}-amino)-N,N'-bis-(2,3-dihydroxy-propyl)-2,4,6-triiodo-isophthalamide The tetraepoxide pentaerytrol tetraglycidylether was prepared according to the procedure of T. Kida, M. Yokota, A. Masuyama, Y. Nakatsuji, M. Okahara: A facile synthesis of polyglycidyl ethers from polyols and epichlorohydrin. Synthesis, (5) 1993, 487-489. At 23-50° C. 5-Acetylamino-N,N'-bis-(2,3-dihydroxy-propyl)-2,4,6-triiodo-isophthalamide (400 g, 535 mmol) was dissolved in a solution of KOH (41.07 g, 731 mmol) in water (431 ml) and methanol (203 ml). To the clear solution boric acid (21.55 g, 348 mmol) was added and stirred for 0,5-3 h. At 10° C. pentaerytrol tetraglycidylether (32.5 g, 90.3 mmol) was added and stirred for 1 d. Boric acid 3,67 g, 59 mmol) was added and stirring continued at 10° C. for one more day. The reaction was stopped by adding water (600 ml) and neutralization with 18.4% aqueous HCl to pH 4-5. A white precipitate (starting material) was filtered and the filter cake washed with water. Salts were removed from the filtrate by ion exchangers Amberlite 200C and IRA67. The solution contains 7 HPLC area% target compound (ca. 16 g) and the product was isolated by prep. HPLC.

HPLC/MS (TOF ES+, m/e): 2619,7 $[M+H]^+$, 1310.3 $[M+2H]^{2+}$.

$^1$H NMR (d6-DMSO): 8.7-8.1 (m, 6H, NH), 4.9-4.2 (m, 17H, OH), 4.1-2.9 (m, 58H, $CH_2$ & CH), 2.2 & 1.75 (s, 9H, $CH_3$).

IR: 3266 (m), 2926 (w), 1641 (vs), 1552 (m), 1396 (m), 1258 (m), 1108 (s), 1038 (s), 979 (w).

EXAMPLE 4

5-(Acetyl-{3-[2,2-bis-(3-{acetyl-[3,5-bis-(2,3-dihyroxy-propylcarbamoyl)-2,4,6-triiodo-phenyl]-amino}-2-hydroxy-propoxymethyl)-3-(3-{acetyl-[3,5-bis-(2,3-dihydroxy-propylcarbamoyl)-2,4,6-triiodo-phenyl]-amino}-2-hydroxy-propoxy)-propoxy]-2-hydroxy-propyl}-amino)-N,N'-bis-(2,3-dihydroxy-propyl)-2,4,6-triiodo-isophthalamide The tetraepoxide pentaerytrol tetraglycidylether was prepared according to the procedure of T. Kida, M. Yokota, A. Masuyama, Y. Nakatsuji, M. Okahara: A facile synthesis of polyglycidyl ethers from polyols and epichlorohydrin. Synthesis, (5) 1993, 487-489. At 23-50° C. 5-Acetylamino-N,N'-bis-(2,3-dihydroxy-propyl)-2,4,6-triiodo-isophthalamide (400 g, 535 mmol) was dissolved in a solution of KOH (41.07 g, 731 mmol) in water (159 ml) and methanol (159 ml). To the clear solution boric acid (25,22 g, 407 mmol) was added and stirred for 0,5-3 h. At 10° C. pentaerytrol tetraglycidylether (32,5 g, 90.3 mmol) was added and stirred for 2 days. The reaction was stopped by adding water (1000 ml) and neutralization with 18,4% aqueous HCl to pH 4-5. A white precipitate (starting material) was filtered and the filtercake washed with water. Salts were removed from the filtrate by ion exchangers Amberlite 200C and IRA67. The solution contains 15 HPLC area % target compound (ca. 45 g) and the product was isolated by prep. HPLC.

HPLC/MS (TOF ES+, m/e): 3348,8 $[M+H]^+$, 1674,9 $[M+2H]^{2+}$.

What is claimed is:
1. Compounds of formula (I)

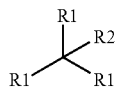

Formula (I)

wherein
each $R^1$ are the same or different and denote the moieties $CH_2$—O—$CH_2$—$R^3$;
$R^2$ denote $R^1$ or one of the moieties $C_1$-$C_4$ alkyl, $CH_2O(C_1$-$C_4$ alkyl) and OH, where the alkyl group may carry one or more hydroxy groups;
each $R^3$ are the same or different and denote a $C_1$-$C_4$ alkylene moiety having α-hydroxy and ω-$NR^4$ R substituents and where the alkylene group may be further hydroxylated;
each $R^4$ are the same or different and denotes a hydrogen atom or an acyl moiety; and
each R independently are the same or different and denote a triiodinated phenyl group where at least one of the R groups is further substituted by a hydrophilic group; and salts or optical active isomers thereof.

2. Compounds as claimed in claim 1 wherein $R^2$ denote a methyl group, an ethyl group or a hydroxylated ether group preferably of the formula —$CH_2$—O—$CH_2$—CH(OH)—$CH_2OH$.

3. Compounds as claimed in claim 1 wherein $R^2$ denote $R^1$.

4. Compounds as claimed in claim 1 wherein each $R^3$ denotes a group of formula —CH(OH)—$CH_2$—$NR^4$R.

5. Compounds as claimed in claim 1 wherein each $R^3$ is the same in all $R^1$ moieties in formula (I).

6. Compounds as claimed in claim 1 wherein $R^4$ is same or different and denote residues of aliphatic organic acids.

7. Compounds as claimed in claim 6 wherein each $R^4$ are residues of aliphatic organic acids of 1 to 5 carbon atoms such as the formic, acetyl, propionyl, butyryl, isobutyryl and valeriyl moieties or the corresponding hydroxylated acyl moieties thereof.

8. Compounds as claimed in claim 1 wherein all $R^4$ groups are the same.

9. Compounds as claimed in claim 1 wherein each group R are substituted by two groups $R^5$ wherein each $R^5$ are the same or different and denotes a hydrogen atom or a non-ionic hydrophilic moiety, provided that at least one $R^5$ group in the compound of formula (I) is a hydrophilic moiety.

10. Compounds as claimed in claim 9 wherein each $R^5$ denote esters, amides and amine moieties, optionally further substituted by a straight chain or branched chain $C_{1-10}$ alkyl groups, optionally with one or more $CH_2$ or CH moieties replaced by oxygen or nitrogen atoms and optionally substituted by one or more groups selected from oxo, hydroxyl, amino or carboxyl derivative, and oxo substituted sulphur and phosphorus atoms.

11. Compounds as claimed in claim 10 wherein each $R^5$ denote esters, amides and amine moieties, optionally further substituted by a straight chain or branched chain $C_{1-5}$ alkyl groups, optionally with one or more $CH_2$ or CH moieties replaced by oxygen or nitrogen atoms and optionally substituted by one or more groups selected from oxo, hydroxyl, amino or carboxyl derivative, and oxo substituted sulphur and phosphorus atoms.

12. Compounds as claimed in claim 11 wherein each $R^5$ are hydrophilic moieties containing 1 to 6 hydroxy groups, preferably 1 to 3 hydroxy groups.

13. Compounds as claimed in claim 12 wherein each $R^5$ may be the same or different and are polyhydroxyalkyl, hydroxyalkoxyalkyl and hydroxypolyalkoxyalky groups attached to the phenyl group via an amide linkage such as hydroxyalkylaminocarbonyl, N-alkyl-hydroxyalkylaminocarbonyl and bis-hydroxyalkylaminocarbonyl groups.

14. Compounds as claimed in claim 9 wherein each $R^5$ are the same or different and are selected from groups of the formulas
—CONH—$CH_2$—$CH_2$—OH
—CONH—$CH_2$—CHOH—$CH_2$—OH
—CON($CH_3$)$CH_2$—CHOH—$CH_2$OH
—CONH—CH—($CH_2$—OH)$_2$
—CON—($CH_2$—$CH_2$—OH)$_2$
—$CONH_2$
—$CONHCH_3$
—$NHCOCH_2OH$
—N($COCH_3$)H
—N($COCH_3$)$C_{1-3}$ alkyl
—N($COCH_3$)— mono, bis or tris-hydroxy $C_{1-4}$ alkyl
—N($COCH_2OH$)— hydrogen, mono, bis or tris-hydroxy $C_{1-4}$ alkyl
—N(CO—CHOH—$CH_2OH$)— hydrogen, mono, bis or trihydroxylated $C_{1-4}$ alkyl,
—N(CO—CHOH—CHOH—CH2OH)— hydrogen, mono, bis or trihydroxylated $C_{1-4}$ alkyl
—N($COCH_2OH$)$_2$
—CON ($CH_2$—CHOH—$CH_2$—OH) ($CH_2$—$CH_2$—OH)
—CONH—C($CH_2$—OH)$_3$ and
—CONH—CH($CH_2$—OH) (CHOH—$CH_2$—OH).

15. Compounds as claimed in claim 14 wherein each $R^5$ are the same or different and are selected from groups of the formulas —CON($CH_3$)$CH_2$—CHOH—$CH_2OH$, —CONH—$CH_2$—CHOH—$CH_2$—OH, —CONH—CH—($CH_2$—OH)$_2$, —CON—($CH_2$—$CH_2$—OH)$_2$, —CONH—$CH_2$—CHOH—$CH_2$—OH, —$NHCOCH_2OH$ and —N($COCH_2OH$)-mono, bis or tris-hydroxy $C_{1-4}$ alkyl.

16. Compound as claimed in claim 15 wherein each $R^5$ are equal and are —CONH—$CH_2$—CHOH—$CH_2$—OH.

17. Compounds as claimed in claim 1 being 5-(Acetyl-{3-[2,2-bis-(3-{acetyl-[3,5-bis-(2,3-dihydroxy-propylcarbamoyl)-2,4,6-triiodo-phenyl]-amino}-2-hydroxy-propoxymethyl)-butoxy]-2-hydroxy-propyl}-amino)-N,N'-bis-(2,3-dihydroxy-propyl)-2,4,6-triiodo-isophthalamide, 5-(Acetyl-{3-[2,2-bis-(3-{acetyl-[3,5-bis-(2,3-dihydroxy-propylcarbamoyl)-2,4,6-triiodo-phenyl]-amino}-2-hydroxy-propoxymethyl)-propoxy]-2-hydroxy-propyl}-amino)-N,N'-bis-(2,3-dihydroxy-propyl)-2,4,6-triiodo-isophthalamide, 5-(Acetyl-{3-[2,2-bis-(3-{acetyl-[3,5-bis-(2,3-dihydroxy-propylcarbamoyl)-2,4,6-triiodo-phenyl]-amino}-2-hydroxy-propoxymethyl)-3-(2,3-dihydroxy-propoxy)-propoxy]-2-hydroxy-propyl}-amino)-N,N'-bis-(2,3-dihydroxy-propyl)-2,4,6-triiodo-isophthalamide, and 5-(Acetyl-{3-[2,2-bis-(3-{acetyl-[3,5-bis-(2,3-dihydroxy-propylcarbamoyl)-2,4,6-triiodo-phenyl]-amino}-2-hydroxy-propoxymethyl)-3-(3-{acetyl-[3,5-bis-(2,3-dihydroxy-propylcarbamoyl)-2,4,6-triiodo-phenyl]-amino }-2-hydroxy-propoxy)-propoxy]-2-hydroxy-propyl}-amino)-N,N'-bis-(2,3-dihydroxy-propyl)-2,4,6-triiodo-isophthalamide.

18. An X-ray diagnostic composition comprising a compound of formula (I) as defined in claim 1 together with a pharmaceutically acceptable carrier or excipient.

19. A method of imaging, specifically X-ray imaging, comprising administration of compounds of formula (I) as defined in claim 1 to the human or animal body, examining the body with a diagnostic device and compiling data from the examination and optionally analysing the data.

* * * * *